US008307745B2

(12) United States Patent
Christensen, III

(10) Patent No.: US 8,307,745 B2
(45) Date of Patent: Nov. 13, 2012

(54) LEVER DEVICE

(75) Inventor: Robert W. Christensen, III, Denver, CO (US)

(73) Assignee: CranioMandibular Rehab, Inc., Denver, CO (US)

( * ) Notice: Subject to any disclaimer, the term of this patent is extended or adjusted under 35 U.S.C. 154(b) by 179 days.

(21) Appl. No.: 12/505,257

(22) Filed: Jul. 17, 2009

(65) Prior Publication Data

US 2010/0011916 A1 Jan. 21, 2010

Related U.S. Application Data

(60) Provisional application No. 61/081,656, filed on Jul. 17, 2008.

(51) Int. Cl.

| | |
|---|---|
| ***B25B 1/04*** | (2006.01) |
| ***B25B 7/12*** | (2006.01) |
| ***A61B 17/60*** | (2006.01) |

(52) U.S. Cl. ............... 81/485; 606/105; 81/342; 81/362

(58) Field of Classification Search .................... 81/485, 81/302, 315, 318, 342, 346, 349, 352–354, 81/362, 363, 416–418; 606/90, 105, 15
See application file for complete search history.

(56) References Cited

U.S. PATENT DOCUMENTS

| | | | | |
|---|---|---|---|---|
| 832,804 | A * | 10/1906 | Mae | 81/349 |
| 1,401,546 | A * | 12/1921 | Mae | 81/353 |
| 2,992,576 | A * | 7/1961 | Evans et al. | 81/354 |
| 6,551,316 | B1 * | 4/2003 | Rinner et al. | 81/352 |
| 7,189,234 | B2 * | 3/2007 | Zucherman et al. | 606/249 |

* cited by examiner

*Primary Examiner* — Hadi Shakeri

(57) ABSTRACT

A lever device includes first and second levers coupled at a lever pivot. First end of a first bar is pivotally coupled to the first lever at a first lever-bar pivot. First end of a second bar is pivotally coupled to the second lever at a second lever-bar pivot. First tool is pivotally coupled to a distal end of the first lever at a first lever-tool pivot. Second end of the first tool is pivotally coupled to the second end of the second bar. Second tool is pivotally coupled to the second lever at a second lever-tool pivot and a second end of the lever is pivotally coupled to the second end of the second bar. First lever-bar pivot is between the lever pivot and a distal end of the first lever and the second lever-bar pivot is between the lever pivot and a distal end of the second lever.

15 Claims, 5 Drawing Sheets

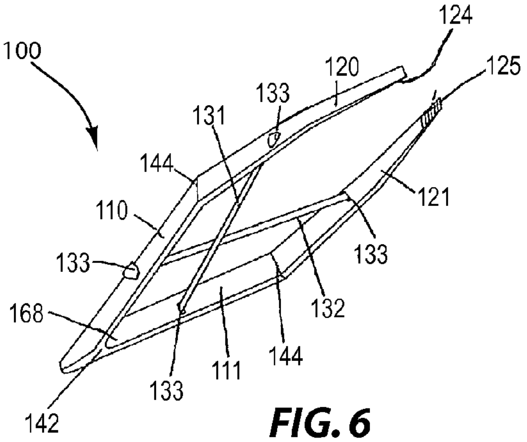
FIG. 6
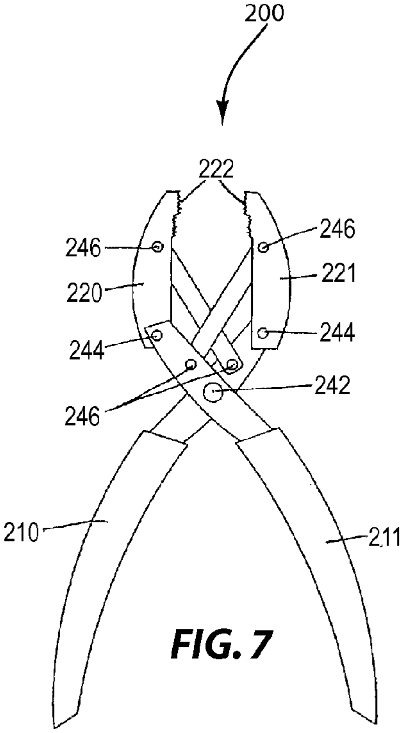
FIG. 7
FIG. 8
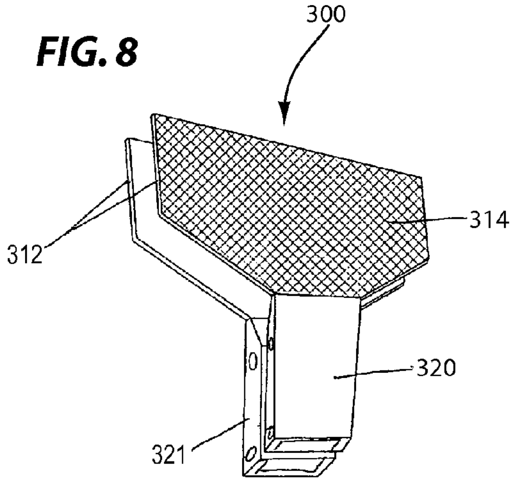

LEVER DEVICE

CROSS-REFERENCE TO RELATED APPLICATIONS

The present application claims the benefit of U.S. Provisional Patent Application Ser. No. 61/081,656 filed Jul. 17, 2008 entitled “Lever Device”, which is hereby incorporated by reference in its entirety.

BACKGROUND

1. The Field of the Invention

This invention generally relates to a lever device that can create a predetermined tool path, specifically to a lever device such as a tool with an arced tool path.

2. The Relevant Technology

A basic pliers structure includes two handles hinged along their body with handles on one end and tool faces on the other. This basic structure opens the tool faces in a path that rotates around the central hinge. A variety of tools work from this basic motion including pliers, wrenches, spreaders, and scissors. Tools have also been developed to change the rotational path to another shape or have added components to provide a different function.

Ring expander pliers, horizontal pliers, and jaw exercisers are an example of tools developed with tool paths different from the rotation of their pivoting handles. Many of these tools use slides and/or arms to change the tool path. However, these devices do not open in an arc with a center in front of the tools.

One type of pivoted hand tool modified to create a different function is the castrating band applying tool of U.S. Pat. No. 2,582,640 (’640 patent). The tool of the ’640 patent has laterally projecting pins on which an elastic band is spread and placed on an animal. The tool of the ’640 patent has jaws which curve inwardly at the front end of its handles with pins extending laterally from them, and has arms pivoted from the side of the handles at the rear portion of the jaws, with an arcurate link pivoted from the handles to the arms. Moving the handles opens and closes the jaws, arms, and pins. When closed, the pins are closely grouped and a band can be placed over them. Moving the handles swings the jaws apart and swings the arms rearwardly into an inclined converging relationship to expand the band for placement over a tail or scrotum. The tool of the ’640 patent does not have tools or arms extending forward from the handles; placing the tool arms forward of the handles would not allow the pins to closely group and would thus render the device dysfunctional. The ’640 patent tool also does not create a declining relation of the tool with its path having a radial point in front of the tool. The ’640 patent also does not show any tools without pins, without jaws on the handles, or with tool faces to be used for non-band-applying uses.

Compound lever devices and locking pliers are other tools with different functions from the basic pliers that utilize alternative structures different from the basic pliers arms. The structure of these tools vary the function but do not alter the tool path.

BRIEF SUMMARY OF THE INVENTION

In at least one example, a lever device such as a pivot tool includes a first lever, a second lever, a first tool and a second tool, and a first bar and a second bar pivotally connected together to create a motion of the tools that is modified from the motion of the levers. The lever device can include a spring to provide force on the device. One example of the lever device such as a jaw exerciser includes mouthpieces as the tools.

In at least one example, a lever device, includes a first lever having a proximal end and a distal end, a second lever having a proximal end and a distal end, the first lever and the second lever being pivotally coupled at a lever pivot, a first bar having a first end and a second end, the first end being pivotally coupled to the first lever at a first lever-bar pivot, a second bar having a first end and a second end, the first end being pivotally coupled to the first lever a second lever-bar pivot, a first tool having a first end and a second end, the first end of the first tool being pivotally coupled to a distal end of the first lever at a first lever-tool pivot and the second end extending distally of the first lever and being pivotally coupled to the second end of the second bar, and a second tool having a first end and a second end, the first end of the second tool being pivotally coupled to the second lever at a second lever-tool pivot and the second end extending distally of the second lever and being pivotally coupled to the second end of the second bar; wherein the first lever-bar pivot is between the lever pivot and the distal end of the first lever and the second lever-bar pivot is between the lever pivot and the distal end of the second lever.

These and other features of the present invention will become more fully apparent from the following description and appended claims, or may be learned by the practice of the invention as set forth hereinafter.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 6 is a perspective view of another embodiment of the lever device in accordance with the present invention.

FIG. 7 is a side view of another embodiment of the lever device; and

FIG. 8 is a perspective view of another embodiment of the lever device tool.

DRAWINGS—REFERENCE NUMERALS

Figure 1:
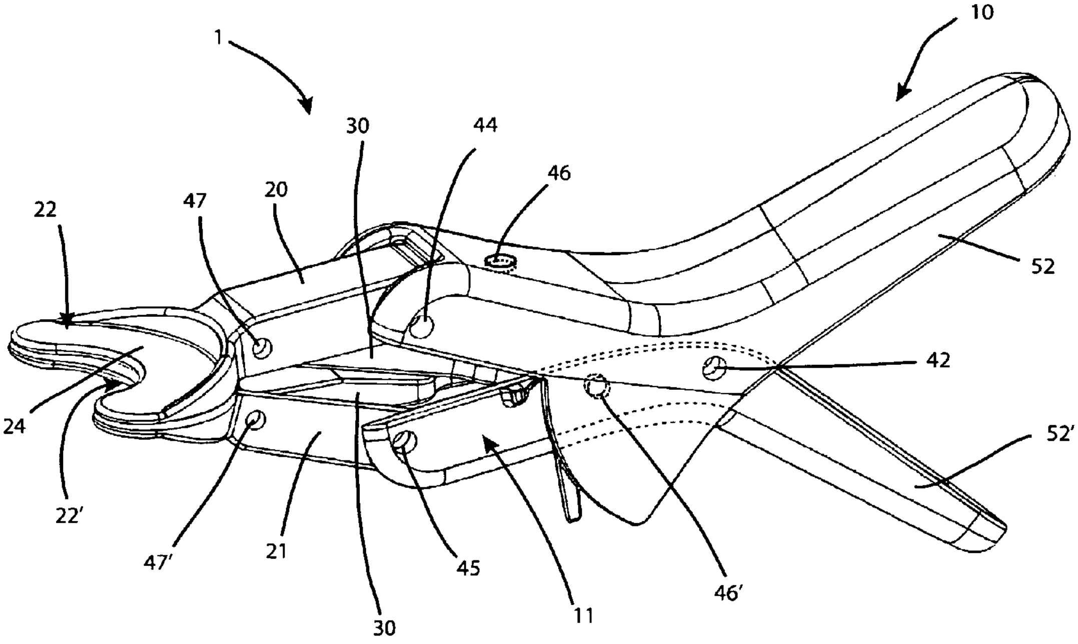
FIG. 1 is a perspective view of an a lever device as a jaw exerciser according to one example.

1 Lever Device
10 Lever
11 Lever
12 Rotation
13 Length
20 Tool
21 Tool
22, 22' Tool structure
24 Tool face
26, 26' Mouthpiece
30 Bar
31 Bar
42 Lever pivot
44 Tool pivot

45 Tool pivot
46, 46' Bar pivot
47, 47' Bar pivot
50 Limit structure
52, 52' Handle
54 Pin
54*a* Pin
56 Loose hole
58 Fitted hole
59 Pivot hole
60 Bite area
62 Occlusal surface
64 Raised wall
66 Pad
68 Spring
70 Spring catch
72 Tool path
72*a-d* Tool paths
74 Handle body
76 Scale
77 Indicia
78 Pointer
80 Threaded hole
82 Screw
84 Screw catch
86 Tab
88 Catch
92, 92' Raised body
94 Hollow Body
95 Recess
96 Curved Tool Path
100 Tweezer tool
110 Lever
111 Lever
120 Tool
121 Tool
124 Tool face
125 Tool face
130 Bar
131 Bar
132 Tab
133 Slot
142 Lever pivot
144 Tool pivot
146 Bar pivot
150 Plastic Hinges
168 Plastic Spring
200 Pliers
210 Lever
211 Lever
220 Tool
221 Tool
222 Gripping surface
230 Bar
231 Bar
242 Lever pivot
244 Tool Pivot
246 Bar Pivot
300 Spreader
312 Vice Face
314 Gripping Surface
320 Tool
321 Tool
322 Vise face
324 Gripping surface

DETAILED DESCRIPTION OF EXEMPLARY EMBODIMENT

A lever device includes a first lever, second lever, first tool, second tool, first bar, second bar, and pivots. The pivots are structures on the levers, tools, and bars that allow the various parts to connect to each other, and to move or rotate in relation to each other; i.e. a pivotal or rotational connection. The pivots can be axis, elbows, joints, hinges, pivoting connectors, or other structures for coupled and/or connected movement of components. The first lever and second lever can be a handle, lever, pivot lever, and/or stiff members to mobilize the device. The first and second levers have pivots along their body, such as a tool pivot at one end, a lever pivot, and a bar pivot between the tool pivot and the lever pivot. The first and second levers are pivoted together at their lever pivot to move or rotate in relation to each other. The first tool and second tool can be a mouthpiece, pliers, vise, tweezer, spreader, speculum, or another body for interacting with external structures. The first and second tools have a tool structure, a bar pivot along its body, and a tool pivot at one end. Each tool extends from and connects to the tool pivot on a corresponding lever. The first bar and second bar can be a crosslink, link bar, swing bar, lever, and/or a beam to connect the levers and tools. The first and second bars have pivots at or near both ends. The first bar is connected at the bar pivot of the first tool, extends past the tool pivot between them, and connects to the bar pivot on the second lever. The second bar is similarly connected to the second tool and the first lever. The lever device moves to create a predetermined path of the tool structures if different from the arcurate path of the tool pivots (with a center at the lever pivot) on the levers.

There are various embodiments of the lever device. One example includes a spring attached to the lever device. Other examples of structures or features include having a pin structure for the pivots; having a mouthpiece as the tool; and having extended levers to act as handles. Other features and components can be added to supplement the lever device for positioning control, safety, and other tool interfaces.

In FIG. 1 an example embodiment of the lever device 1 is illustrated. The lever device 1 includes a first lever 10 and second lever 11 connected at a lever pivot 42 along their bodies. Divided by the lever pivot 42, one side of the each lever has a tool pivot 44, 45 at or near its corresponding end, and a bar pivot 46, 46' between the tool pivot 44, 45 and the lever pivot 42. The bar pivot 46, 46' on the levers 10, 11 can be positioned as part of the lever pivot 42. The other side of each lever 10, 11 is extended at an angle past the lever pivot 42 to form a handle 52, 52' or an area for gripping by a user. In this example, the levers 10, 11 are V-shaped along their cross-section with the lever pivot 42 at their vertex.

The lever device 1 includes a first tool 20 and a second tool 21 with tool structures 22, 22' having tool faces 24, 24' a bar pivot 47, 47' positioned on their bodies, and the tool pivot 44, 45 at an end. The first and second tools 20, 21 are connected to the first and second levers 10, 11 respectively at the tool pivots 44, 45.

A first bar 30 connects to the first lever 10 at the bar pivot 46 and extends across the tool pivot 44 to connect to the second tool 21 at the bar pivot 47'. A second bar 31 connects to the first tool 20 and second lever 11 at their bar pivots 46, 47.

In this example, some structures are identical or very similar between the pairs of levers 10, 11, tools 20, 21 and bars 30, 31 like the various pivots 42, 44, 45, 46, 46' 47, 47' the tool structures 22, 22' and handles 52, 52' and are labeled with the similar numbers for the sake of simplicity and to highlight the basic structure of the lever tool. However these structures can be different in other embodiments of the lever device 1.

Figure 2:
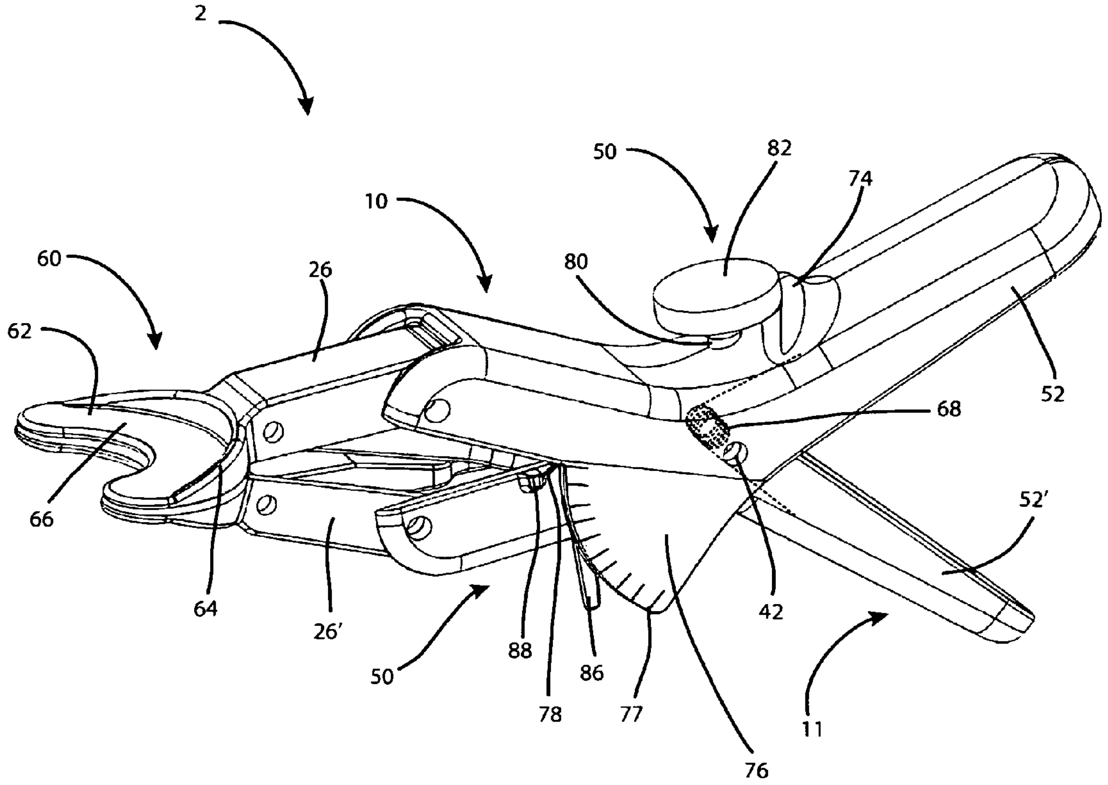
FIG. 2 is another perspective view of an embodiment of the jaw exerciser in accordance with the present invention.

FIG. 2 illustrates further features of a lever device 1 as a jaw exerciser. The levers 10, 11 extend past the lever pivot 42 as handles 52, 52'. The tools 20, 21 are mouthpieces 26, 26' that include a bite area 60 having an occlusal surface 62 that can include a pad 66 applied to it, and a raised wall 64 or other structure for dental retention. The pad can be a cushion, coating, moldable insert, or other material for the cushioning or retention of teeth attached or applied to the bite area 60. The opposing tool 26' can be a mirror image of tool 26 or can be different.

A spring 68, elastic component or other structure for continuous force, illustrated here as a torsional spring, is located between the levers 10, 11 at the lever pivot 42.

A scale 76 is shown on one side of lever 10 with a corresponding pointer 78 positioned on the other lever 11. The pointer 78 can be labels, decals, structures, or other indicators capable of signaling position on the scale 76. The scale 76 has indicia 77 on it, shown as lines positioned along the scale 76. The scale 76 illustrated here has an extended curved body down one side on the first lever 10. A pointer 78 is shown as a triangle extrusion on the second lever 11. As the levers 10, 11 rotate in relation to each other, the indicia 77 move in relation to the pointer 78, indicating a distance of motion of the lever device 1. The indicia 77 can be positioned to correspond to the distance between the tools.

The lever device 1 further includes limit structures 50, which can be a screw 82, a tab 86, or other body for stopping or controlling the motion of the device. One example of a limit structure 50 includes a screw 82 and a threaded hole 80 on one lever 10, as illustrated in FIG. 2. The screw 82 can be inserted through the threaded hole 80 to hit the other lever 11, to act as a stop or limit on the opening distance of the lever device 1. Additionally, a handle body 74, such as a finger wall, ergonomic structure or other body to improve the holding of the lever device 1, is shown along the lever 10.

Another example of a limit structure 50 includes a tab 86, or other extending member, on one lever, to interfere with another component and movement of the lever device 1. Illustrated in FIG. 2, the tab 86 extends out from the scale 76 to hit a catch 88 on the side of the other lever 11. This structure limits maximum opening distance to the jaw exerciser, and can be cut off to allow full motion as desired.

Figure 3:
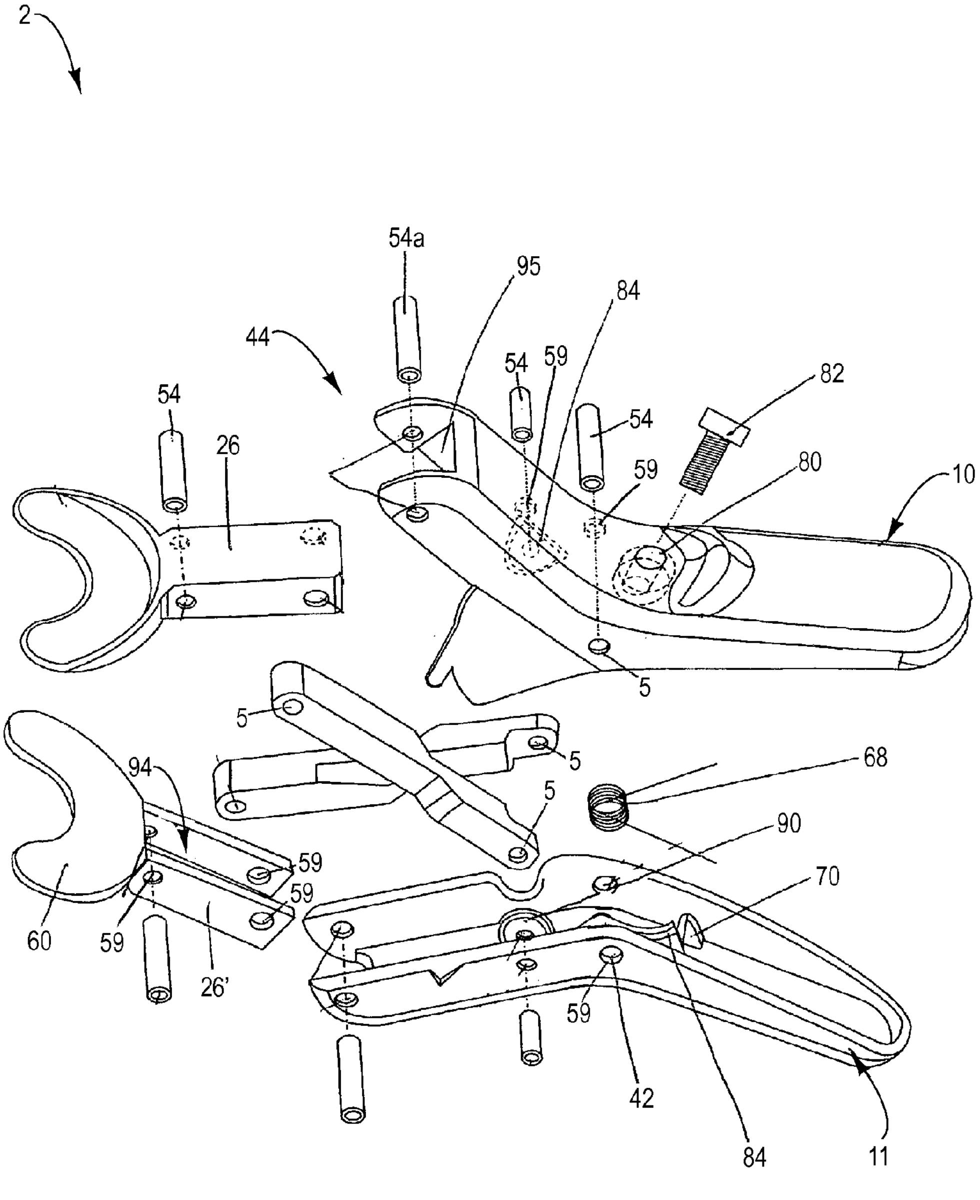
FIG. 3 is an exploded view of the jaw exerciser in accordance with the present invention.

FIG. 3 illustrates further features of this example embodiment of the lever device 1 as a jaw exerciser in an exploded view.

The pivots 42, 44, 45, 46, 46' 47, 47' of this example embodiment all have similar structures with pins 54 and pivot holes 59; however the pivots 42, 44, 45, 46, 46' 47, 47' and their components are of different lengths and widths based on the overall structure and sizes necessary. For simplification of the specification, one example of this type of pivot is discussed at the tool pivot 44 formed between the first lever 10 and the first tool 20. In this tool pivot 44, the lever 10 is wider than the tool 20 and has a recess 95 defined herein. The tool 20 is positioned within the recess 95 of the lever 10 at an end that is configured to connect with the tool 20. The lever 10 has fitted holes 58 on each of its sides. The tool 20 has loose holes 56 on both of its sides. The pin 54*a* is sized to move freely within the loose holes 56 and to be retained within the fitted holes 58. In the tool pivot 44, the tool 20 and lever 10 are positioned with their holes 56, 58 aligned, and the pin 54*a* is inserted through the holes 56, 58 to form the tool pivot 44. The tool pivot 45 between the lever 11 and the tool 21 can have substantially the same structure as the tool pivot 44. Similar pivot structures can be used at the lever pivot 42 between with the second lever 11 within the first lever 10; at the bar pivots 46, 46' between the bars 30, 31 and the levers 10, 11, and the bar pivots 47, 47' between the bars 30, 31 and the tools 20, 21. The pins 54, 54*a* can be a solid, rolled, coiled or spring pin, a rivet, a bolt and nut, or other structure known by one skilled in the art for the rotational connection of two components.

The tools 20, 21 are configured with three-sided recess 95 extending from the bite area 60, to allow the bars 30, 31 to fit between the tools 21. The first lever 10 can be wider than the second lever 11. Both levers 10, 11 are configured with three sides to be open, with the second lever 11 fitting into the first lever 10, and aligned to form the lever pivot 42 (FIG. 1). The first and second levers 10, 11 have a raised body 92 within them as part of the bar pivot 46 (FIG. 1). The raised bodies 92, 92' and the sides of the levers 10, 11 have pivot holes 59 for pins 54 to be inserted through to form the bar pivots 46, 46'.

In the lever 11 is defined a screw catch 84 opposite the threaded hole 80 (in lever 10) in a curved configuration to provide a perpendicular surface to the screw 82 as it rotates with the lever 10. Each lever 10, 11 also contains a spring catch 70 aligned with and holding the spring 68 in place.

Figure 4:
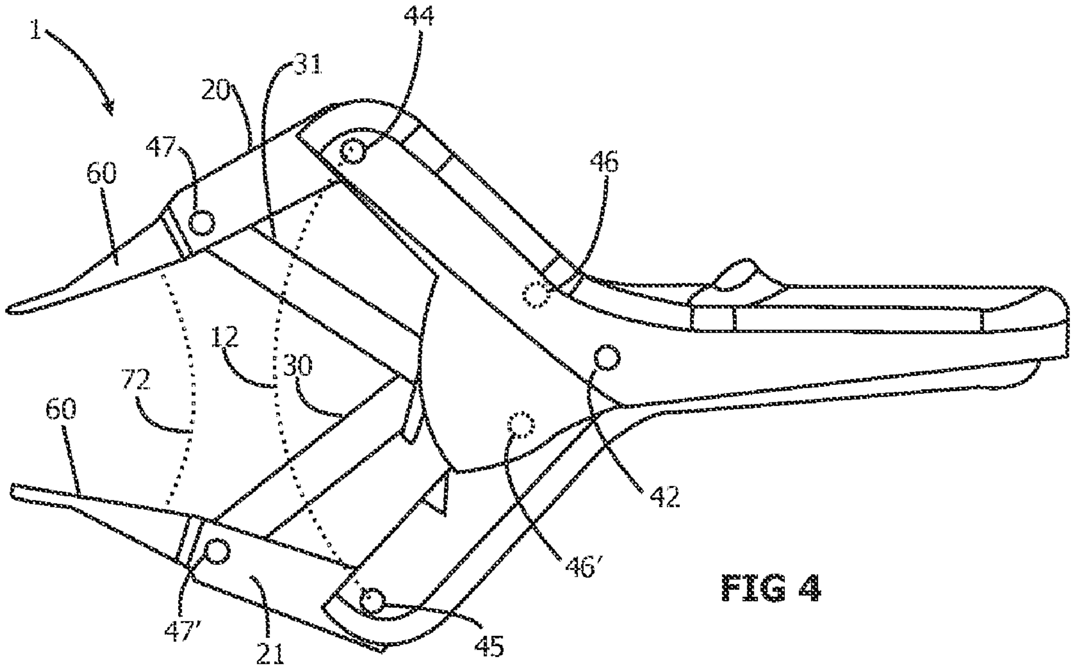
FIG. 4 is another perspective view of an embodiment of lever device in accordance with the present invention.

FIG. 4 illustrates the predetermined tool path 72 of the lever device 1 and the rotation 12 of the tool pivots 44, 45. The tool pivots 44, 45 move away from each other in a rotation 12 that is a path centered at the lever pivot 42 and having a radius equal to the distance between the lever pivot 42 and the tool pivots 44, 45. The tool path 72 of the lever device 1 is different from the lever rotation 12. The bars 30, 31 control the path 72 of the tools 20, 21 by rotating them separately from ends of the levers 10, 11. The length of the bars 30, 31 and position of the bar pivots 46, 47 determines how the tools 20, 21 will move in relation to the levers 10, 11. The shape of the tool path 72, with some of the various possibilities shown in FIGS. 5*a*, 5*b*, 5*c*, and 5*d*, are determined by the length of the bars 30, 31 and the location of the bar pivots 46, 46', 47, 47'. The size of the tool path 72 is determined by the overall length and size of all the components of the lever device 1.

The length of the bars 30, 31 control how much a tool 20, 21 is pulled toward the opposite tool 21, 20: the shorter the bars 30, 31 are, the more the tools 20, 21 are pulled to change the tool path 72. Additionally, the location of the bar pivot 46 on the levers 10, 11 and the bar pivot 47 on the tools 20, 21 affects the shape of the path as well. The further the bar pivot 46 is from the lever pivot 42; the more the tools 20, 21 are pulled toward each other. And the closer the bar pivots 47, 47' are to the tool pivots 44, 45, the more the tools 20, 21 are pulled toward each other. Adjusting the length of the bars 30, 31 and locations of the bar pivot 46; shapes possible paths 72 for each tool 20, 21: some are curved toward the levers, straight, and reverse curved. The tool path 72 can be designed as simple circular arcs, but can also create more complex functional paths as curves, arcs, lines and other shaped paths. The general crossed bar design of the lever device 1 to create a curved tool path 72 can be used in devices from miniature apparatus to large hydraulic tools by adjusting the overall size of the device or its components.

One benefit of lever tool's 1 tool path 72 is in its use as a jaw exerciser. The tool path 72 of the jaw exerciser moves similar to that of the jaw and teeth. By mimicking the motion of an opening jaw and mouth, the bite areas 60 move with a users dentition to engage and support a broader area of the teeth, which spreads the pressure, reduces pain and damage, and provides more area for engagement against users teeth. This example lever device 1 as a jaw exerciser 2 for humans should be sized to create a curved tool path 96 for human jaws of about 2 to 7 inches in radius and of a distance up to 4 inches long; and with handles 52 of size to be held within a human hand.

FIGS. 5*a*, 5*b*, 5*c* and 5*d* illustrate the various tools paths 72 that can be created by the lever tool 1. The tool path 72 is determined by length of the bars 30, 31, in relation to the shape of the levers 10, 11 and tools 20, 21, and the location of and distance between the lever pivot 42, the lever-bar pivots 46, 46' on the levers 10, 11, and the tool-bar pivots 47, 47' on the tools 20, 21. These relations further determine the location of the tools 20, 21 when the device 1 is in a closed position, such that the tools 20, 21 may lay flat against each other, touch only at their ends, or not touch at all, with the device 1 in a closed position. FIGS. 5*a*, 5*b*, 5*c*, and 5*d* are examples of how these relations change the tool path 72 of the device 1.

Figure 5A:
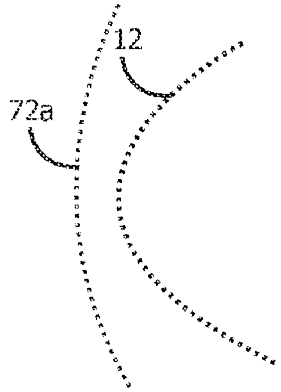
FIGS. 5*a, b, c,* and *d,* are views of motion paths of the lever device.
Figure 5B:
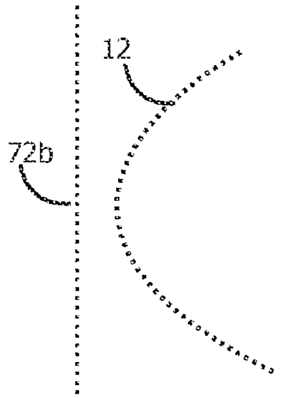
Figure 5C:
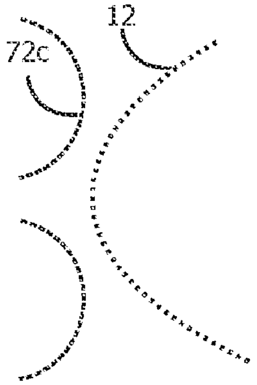
Figure 5D:
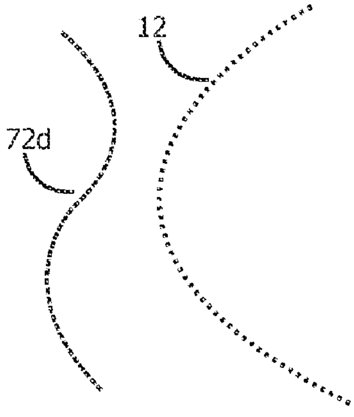

FIG. 5*a* illustrates a tool path 72*a* similar to the rotation 12 of the levers 10, 11. This shape path 72*a* would be created with longer bars 30, 31, a bar pivot 46 near the lever pivot 42, and a bar pivot 47 away from the tool pivot 44. FIG. 5*b* illustrates a tool path 72*b* that is approximately vertically straight to create a parallel opening tool device. The straight tool path 72*b* is created near a functional limit where the curve defined from the length of the bars 30, 31 and bar pivots' 46, 47 has no or a very distant focal point. FIG. 5*c* illustrates a tool path 72*c* with a center in front of the tools 20, 21 to create a path 72*c* opposite, reversed or inverse to the curve of the lever rotation 13. FIG. 5*c* also illustrates a path 72*c* where the tools 20, 21 do not come into contact when the lever device 1 is closed leaving a divide in the middle of the path. This tool path 72*c* can be created from shorter bars 30, 31, and bar pivots 46, 47 further from the lever pivot 42 and closer to the tool pivot 44. FIG. 5*d* illustrates a tool path 72*d* where each tool 20, 21 has a different path, which would be created with each bar 30, 31 having a different length, and/or having bar pivots 46, 47 located in different positions on the levers 10,11 and/or tools 20, 21.

The following dimensions are examples of one embodiment of the lever device 1, and other dimensions can be used. The illustrated example as a jaw exerciser 2 is approximately 8" long when assembled. In this embodiment, the outer lever is 6¾" long and about 1½" wide; and the inner handle 52 is 6" long and about 1⅛" wide. Both levers 10, 11 have a lever pivot 42 along their middle about 2.75" from the end with the tool hinge. The bar pivot 44 is ⅞" away from the lever pivot 42, and the tool pivot 44 is 1¾" from the lever pivot 42. The mouthpiece 26 tool is about 3" in length, with a 2¼" wide bite area 60 for the tool structure 22. The mouthpiece 26 has a ⅝" face around an approximately ¾" radius curve. Each tool extends about 1¾" from the tool structure 22 with the bar pivot 44 about ¼" away from the bite area 60 and the tool pivot 44 about ¼" away from the other end. The bars 30 are about 3¼" long with the bar pivots 46 about ⅜" away from each end. These lengths work to create a tool path 72 with a radius of approximately 5" at the back of the bite area 60 where a user's front teeth would engage. Changing the dimensions to a predetermined length could create different radiuses for larger and smaller mouths found both in humans and in other animals, like babies, dogs or horses.

This example of the lever device 1 as a jaw exerciser 2 functions under the force of the spring 68 and the squeezing of the handles 52 on the levers 10, 11. The V-shape of the handles function to rotate the tools 20, 21 away from each other for use of the lever device 1 as a spreader. By squeezing the handles 52, the user rotates the levers 10, 11 around the lever pivot 42 bringing the handles 52 closer together and moves the tool pivots 44, 45 away from each other. Simultaneously, the levers 10, 11 move the bars 30, 31. The bars 30, 31 lift and pivot each tool 20, 21 at the bar pivots 46. This motion creates the curved tool path 72 with a center in front to the tools 20, 21 and not centered at the lever pivot 42. In the lever device 1 as a jaw exerciser, this curved tool path 72 is used to move the bite areas 60 for the therapy and stretching of the mouth and jaw.

The spring 68 provides a counter force against the squeezing of the handles 52, 52'. In the illustrated example, the spring 68 pushes the levers 10, 11 apart and the tools 20, 21 together when none or insufficient force is applied to the handles 52, 52'. The spring 68 also acts as a damper on the force applied to and by the user. The spring 68 is not required for the device to function, but acts to support the device and would provide a counter pressure to the squeezing of the levers 10, 11. The strength of the spring 68 can be predetermined to reduce the overall force pushing the mouthpieces 26 apart as a safety precaution to prevent the application of excessive force on the user's jaw. Alternatively, the spring 68 can be placed to push the tools 20, 21 apart to create a dynamic constant forced opening of the lever tool 1.

Additionally, limit structures 50 have been added to this example of the present invention. The limit structure 50 with a screw 82 acts as a variable mechanical stop on the movement of the levers 10, 11 to provide a maximum distance of the tool path 72. The stop and maximum distance can be changed by turning the screw 82 to adjust its length through the lever 10 to hit and obstruct the full motion of the other lever 11. A tab 86 and catch 88 is another limit structure 50 that has been added as a safety stop on the device to prevent accidental excessive opening of the lever device 1. The tab 86 can be snapped or cut off to allow the full motion of the lever device 1.

FIG. 6 shows another embodiment of the lever device configured as a tweezer tool 100. The tools 120, 121 have a tweezer tool face 124, 125 on one end and are connected to the levers 110,111 at a tool pivots 144, here shown as plastic hinges. This example shows the levers 110, 111 that connect at the lever pivot 142 as a plastic hinge; and which do not extend past the pivot 142. The bars 130,131 are shown as thin flat rods with tabs 132 at both ends. This example shows the bar pivots 144 as a structure of slots 133 in the levers 110,111 and tools 120,121, where the tabs 132 on the bars 130,131 are inserted through. The tabs 132 are of predetermined shape to squeeze through the slots 133 and catch to prevent sliding back out. The bars 130,131 then rotate within the slots 133 to act as the pivot. The lever pivot 142 in this example also acts as a flat plastic spring holding the levers 110,111 apart.

The example illustrated in FIG. 6, functions with the plastic spring hinge lever pivot 142 holding the levers 110,111 and the tools 120,121 apart. A user can squeeze the levers 110,111 together to move the tools 120,121 and the tweezers tool faces 124, 125 together in a predetermined path that is less than the movement of the lever ends at the tool pivots 144. This example illustrates a lever device 1 without the levers 110,111 extending beyond the lever pivot 142. A lever device 1 as a tweezer tool 100 offers a user a smaller tool distance at its end with a wider distance at its levers 110,111, which translates the wider lever movements to the closer ends for use with tight tolerances or delicate components. The tweezer faces 124, 125 are one of various gripping tool faces possible for use of the lever device 1, the gripping tool faces being configured with a surface to increase friction or deformation of the object being acted on by the tools, like pads, notches, ridges, walls, or an applied coating.

FIG. 7 illustrates an example of lever device configured as pliers 200. This example has a first lever 210 and second lever 211 pivoted together at the lever pivot 242. First and second tools 220, 221 have a tool structure of a gripping surface 222 at one end, a bar pivot 246 along the tool 220, 221 and a tool pivot 244 at the other end connecting them to the levers 210, 211. This example shows the gripping surface 222 on each tool 220, 221 as pliers teeth, and can be shaped into a rectangular face, needle-nose face, wrench face, or other shape to grasp objects, with gripping notches or grooves on it. A first and second bar 230,231 extend and cross from the levers 210, 211 to the opposite bars 230, 231, connecting them at the bar pivots 246. The pivots 242, 244, 246 could be made up of a screw and bolt or rivets through holes in the levers 210, 211, tools 220, 221, and bars 230, 231.

Squeezing the levers 210, 211 rotates them around the lever pivot 242 to move the tools 220, 221 closer together in a predetermined path. The lever device 1 as a pliers 200 can be used to create specific gripping tool paths, like a parallel path without the use of slide structure, or could be used in places where the smaller distance between the tools is advantageous, or to grip specifically shaped objects across a broader face.

FIG. 8 illustrates another example of the tools in a lever device to create a spreader 300 or vise. FIG. 8 shows two tools 320, 321 with large broad tool faces as a vise face 312 facing away from each other. The vise face 312 is broad and is shown with a vise gripping surface 314, which could have ridges, notches, walls, teeth, or an applied material like foam or plastic. As illustrated in FIG. 8, the vise face 312 on the tools 320, 321 are facing away from each other, which creates a lever device as a spreader 300 to push objects apart along a predetermined path. If the tools were set to face toward each other, they would create a squeezing vise that follows the predetermined path of the tools. Using the lever device 1 as a spreader 300 to push objects apart in a predetermined path can better match the objects structure and/or capacity, and support them across a wider surface area. Alternatively, a smooth faced tool could be used to spread biological tissues for other medical uses.

In the various embodiments, the parts can be made of metal or hard plastic like ABS, PE, nylon, acrylic, polypropylene or urethane plastics, with mouthpieces being of a material suitable for oral use. However, these parts can consist of any other material that is sufficiently stiff and safe such as plastic, laminated fibrous materials, other plasticized materials, wood, metal, or any other known to one skilled in the art. The springs can be made of metal or plastic, as coils, torsion springs, flat springs, wire, stamped, strip and flat forms, or any other kind as known to one skilled in the art to provide a force within the lever device.

The above description contains many specifics that should not be construed as limitations on the scope of the invention, but as exemplifications of the various embodiments. Many other ramifications and variations are possible within the teachings of the invention. Alternative embodiments of the lever device include variations of the tool with alternative mouthpiece shapes, alternative tool structures, and tool structures that could be releasable, interchangeable, or moveable. In alternative embodiments the arms could be ergonomically shaped for improved comfort and aesthetic appeal; they could be wrapped or enclosed by a body or case; they could be designed for right- or left-handed versions; and they could be of various lengths and widths. In alternative embodiments the limit structure could be moved to the tool or bars. Other alternative embodiments could include a digital, mechanical, or hydraulic drive, motor, or press, to move the device.

While the above description contains many specifics, the present invention may be embodied in other specific forms without departing from its spirit or essential characteristics. The described embodiments are to be considered in respects only as illustrative and not restrictive. The scope of the invention is, therefore, indicated by the appended claims rather than by the foregoing description. Changes which come within the meaning and range of equivalency of the claims are to be embraced within their scope

The invention claimed is:

1. A lever tool device, comprising:

a first lever having a proximal end and a distal end;

a second lever having a proximal end and a distal end, the first lever and the second lever being pivotally coupled at a lever pivot;

a first bar having a first end and a second end, the first end being pivotally coupled to the first lever at a first lever-bar pivot, the first lever-bar pivot located between the lever pivot and the distal end of the first lever;

a second bar having a first end and a second end, the first end being pivotally coupled to the second lever at a second lever-bar pivot, the second lever-bar pivot located between the lever pivot and the distal end of the second lever;

a first tool having a first end and a second end, the first end of the first tool being pivotally coupled to said distal end of the first lever at a first lever-tool pivot, the second end of the first tool extending distally of the first lever, the first tool being connected by a fixed pivot to the second end of the second bar;

a second tool having a first end and a second end, the first end of the second tool being pivotally coupled to said distal end of the second lever at a second lever-tool pivot, the second end of the second tool extending distally of the second lever, the second tool being connected by a fixed pivot to the second end of the first bar;

wherein the first tool and the second tool are a mouthpiece, the mouthpiece having a bite area on their second end, the bite area having an occlusal surface located on a side of the mouthpiece that faces away from the corresponding surface of the other tool, and wherein the first tool, the second tool, the first bar, the second bar, the first lever, and the second lever are of predetermined sizes, and the lever pivot, the first lever-bar pivot, the second lever-bar pivot, the first tool-bar pivot, and the second tool-bar pivots, are predetermined distances apart, the lever device being configured to produce an arcuate path of the first tool and the second tool convex to the lever pivot upon movement of the first lever in relation to the second lever.

2. The device of claim 1, wherein the proximal end of the first lever and the proximal end of the second lever extend proximally of the lever pivot.

3. The device of claim 1, wherein at least one of the first tool and the second tool further include a gripping face, the gripping face having at least one of a notch, pad, ridge, groove, wall, and applied coating.

4. The device of claim 1, further including a limit structure connected to at least one of the levers, bars, and tools, the limit structure configured to prevent full motion of the lever device.

5. The device of claim 1, further including a scale connected to at least one of the levers, bars, and tools, the scale having indicia and configured to show the distance of the relative separation of the first tool and the second tool.

6. The device of claim 1, further including a spring element to the device, whereby the spring applies dynamic force to move the device to a structural static state.

7. A method of arranging a lever device, comprising:

pivotally connecting a first lever and a second lever together at a lever pivot, the first and second lever each defining a distal end and a proximal end;

pivotally connecting a first end of a first tool to the distal end of the first lever at a first lever-tool pivot;

pivotally connecting a first end of a second tool to the distal end of the second lever at a second lever-tool pivot;

pivotally connecting one end of a first bar at a fixed pivot to the first tool and the other end of the first bar to the second lever between the lever pivot and the second lever-tool pivot, the first bar spanning across the first lever-tool pivot;

pivotally connecting one end of a second bar at a fixed pivot to the second tool and the other end of the second bar to the first lever between the lever pivot and the first lever-tool pivot, the second bar spanning across the second lever-tool pivot;

forming the first tool and the second tool as a mouthpiece, the mouthpiece having a bite area on a second end of the tools, the bite area having an occlusal surface located on a side of the mouthpiece that faces away from the corresponding surface of the other tool; and wherein the first bar and the second bar are of preconfigured length to move the first tool and the second tool in an arcuate motion in relation to each other, the arcuate motion of the tools having a focal point located away from the pivotal connections of the lever device.

8. The method of claim 7, further including connecting a first handle to the first lever and a second handle to the second lever from the pivotal connection between the two levers.

9. The method of claim 7, further including forming at least one of the first and second tools to include a gripping face, the gripping face having at least one of a pad, notches, ridges, walls, and applied coating.

10. The method of claim 7, further including attaching a scale on at least one of the first lever, the second lever, the first tool, and the second tool, the scale having indicia indicating relative separation J between the first tool and the second tool.

11. The method of claim 7, further including attaching a spring element to the device, whereby the spring applies dynamic force to move the device to a structural static state.

12. A lever tool device for exercising the jaw with an arcuate tool motion corresponding to the motion of the users jaw, comprising:

a first lever and a second lever with each having a handle end and a tool end, and a lever pivot connecting the first lever and the second lever between the handle end and the tool end of the each lever, the handle ends shaped to be held within a hand;

a first bar having a tool end and a lever end, the lever end being pivotally coupled to the first lever at a first lever-bar pivot between the lever pivot and the tool end of the first lever;

a second bar having a tool end and a lever end, the lever end being pivotally coupled to the second lever at a second handle lever-bar pivot between the lever pivot and the tool end of the second lever;

a first mouthpiece having a tool arm and a bite area, one end of the tool arm being pivotally coupled to a tool end of the first lever at a first lever-tool pivot, the tool arm extending from the first lever-tool pivot to the bite area, the second bar being pivotally coupled to the tool arm of the first mouthpiece between the first lever-tool pivot and the bite area;

a second mouthpiece having a tool arm and a bite area, one end of the tool arm being pivotally coupled to a tool end of the second lever at a second lever-tool pivot, the tool arm extending from the second lever- tool pivot to the bite area, the first bar being pivotally coupled to the tool arm of the second mouthpiece between the first lever-tool pivot and the bite area;

wherein the lever device is configured to have the handle ends of the levers apart when the mouthpieces are together and to provide motion of the mouthpieces apart in an arcuate path, whereby the path is shaped convexly to the lever pivot.

13. The device of claim 12, further comprising a limit structure attached to the lever tool device, whereby the limit structure acts to restrict the lever device to a range of motion less than the full motion possible by the structure.

14. The device of claim 12 further comprising a scale connected to the lever tool device, the scale showing the distance between the first and second mouthpiece.

15. The device of claim 12 further comprising a spring structure connected to the lever tool device, whereby the spring structure provides dynamic force.

* * * * *